US008515704B2

(12) United States Patent
Son et al.

(10) Patent No.: US 8,515,704 B2
(45) Date of Patent: Aug. 20, 2013

(54) CALIBRATING BREATHALYZER

(75) Inventors: Matthew Hogyun Son, Palisades Park, NJ (US); Jung Hoon Son, Palisades Park, NJ (US)

(73) Assignee: AK Globaltech Corp., Palisades Park, NJ (US)

( * ) Notice: Subject to any disclaimer, the term of this patent is extended or adjusted under 35 U.S.C. 154(b) by 0 days.

(21) Appl. No.: 13/541,787

(22) Filed: Jul. 5, 2012

(65) Prior Publication Data

US 2013/0103340 A1 Apr. 25, 2013

Related U.S. Application Data

(63) Continuation of application No. 13/426,455, filed on Mar. 21, 2012, now Pat. No. 8,224,608.

(60) Provisional application No. 61/550,910, filed on Oct. 24, 2011, provisional application No. 61/563,706, filed on Nov. 25, 2011.

(51) Int. Cl.
*G06F 19/00* (2011.01)
(52) U.S. Cl.
USPC .......................................................... 702/104
(58) Field of Classification Search
USPC .................................... 702/104, 19, 182–185
See application file for complete search history.

(56) References Cited

U.S. PATENT DOCUMENTS

| | | | |
|---|---|---|---|
| 3,552,930 A | 1/1971 | Borkenstein | |
| 5,020,628 A | 6/1991 | Bigliardi et al. | |
| 5,157,601 A | 10/1992 | Jones et al. | |
| 5,239,492 A | 8/1993 | Hartwig et al. | |
| 6,017,308 A | 1/2000 | Fults | |
| 7,841,224 B2 | 11/2010 | Son | |
| 2004/0239510 A1 | 12/2004 | Karsten | |
| 2006/0016244 A1 | 1/2006 | Duval | |
| 2008/0000452 A1 | 1/2008 | Allen et al. | |
| 2010/0138166 A1 | 6/2010 | Do et al. | |
| 2013/0027209 A1* | 1/2013 | Carroll et al. | 340/576 |

FOREIGN PATENT DOCUMENTS

| | | |
|---|---|---|
| WO | WO-02/077636 A2 | 10/2002 |
| WO | WO-2005/101281 A2 | 10/2005 |
| WO | WO-2009/026381 A2 | 2/2009 |

OTHER PUBLICATIONS

US Dept. of Transportation, Office of Program Development and Evaulation, National Highway Traffic Safety Administration, "Computing a BAC Estimate," Oct. 1994, Washington, DC.

* cited by examiner

*Primary Examiner* — Edward Raymond
(74) *Attorney, Agent, or Firm* — IM IP Law PLLC; C. Andrew Im

(57) ABSTRACT

The calibrating breathalyzer comprises an alcohol sensor, a non-volatile memory, a processing unit or processor, a display and a housing to house these components. The processing unit can calibrate the breathalyzer using the user's body as a simulator based on the user's metabolism rate, type and amount of alcohol consumed by the user. The processing unit determines a sample time to receive a breath sample from the user based on a time to a predetermined calibration point from the drinking start time calculated using the user's metabolism rate and the determined maximum alcohol level. The BAC % measurement based on the user's breath sample at the sample time is used as a reference point in calibrating the breathalyzer.

20 Claims, 5 Drawing Sheets

CALIBRATING BREATHALYZER

RELATED APPLICATION

The present application is a continuation of U.S. application Ser. No. 13/426,455 filed Mar. 21, 2012, which claims the benefit of U.S. Provisional Application Ser. Nos. 61/550,910 filed Oct. 21, 1011 and 61/563,706 filed Nov. 25, 2011, each of which is incorporated herein by reference in its entirety.

FIELD OF THE INVENTION

The claimed invention relates generally to a breathalyzer, more specifically to a calibrating breathalyzer and an apparatus for calibrating a breathalyzer using the user's body as a simulator.

RELATED ART

The availability and accessibility of the breathalyzer for both professional use (as in clinical, industrial, healthcare or workplace settings) and personal use (as in the domain of general consumers) has been expanding greatly, and with this expansion the necessity for all breathalyzers to be periodically recalibrated has created many interruptions in the market, as breathalyzers must currently be mailed or delivered to select service center locations where calibration can be done using a simulation system, making the breathalyzer unavailable to the user during this calibration period, and increasingly overwhelming the service centers as the market grows. The claimed invention remedies this situation by providing a method to calibrate (or re-calibrate) the breathalyzer that greatly reduces or even eliminates the time and cost involved in shipping and handling of breathalyzers and maintenance of service centers, as well as the time and utility lost by the end user.

A typical breathalyzer consists primarily of an alcohol sensor component, processing unit (or CPU), and a display unit to show results. Typically, a breath alcohol sensor is calibrated to match select calibration points using standard specifications (controlled alcohol solutions), and the processing unit (or CPU) determines BAC % based on linear calculation using the calibration points. Over time and usage (generally after several hundred tests and or after certain period of time passed), every breath alcohol sensor will require re-calibration as undesirable residue and foreign substances including, but not limited to, saliva, cigarette smoke residue and food particles, change electrical value of the alcohol molecule detected by the sensor. The current system of calibration (or re-calibration) of breathalyzers by service centers takes place when a consumer or end user, with a breathalyzer in need of calibration, contacts a breathalyzer retailer. The retailer, in turn, directs the end user to ship the breathalyzer to an appropriate service center location. Upon receiving the breathalyzer, the service center uses controlled alcohol solutions in order to re-calibrate the device according to standard specifications. When this re-calibration is complete, the breathalyzer is shipped back to the end user. This procedure for re-calibration is time-consuming and costly in terms of shipping and handling of packages, labor hours and lost utility for the end user. There are currently over 100 retailers (online and offline) and/or distributors sell breathalyzer units to consumers and end users, whereas fewer than ten (10) service center locations exist to perform traditional breathalyzer re-calibrations. Due to this discrepancy, the overall increase in sales of breathalyzer units are overwhelming the service centers with requests for re-calibration (which are both necessary and periodic for each breathalyzer), causing ever increasing delays in the processing and delivery of breathalyzers.

Typically, the breathalyzer is calibrated using a simulator with standard alcohol solution(s), or with a dry gas cylinder. Both methods require special tool and standard solutions or gas to calibrate the breathalyzer. Accordingly, the end users must send their breathalyzers to third-party service center for calibration of their breathalyzers or purchase the special tools, e.g., a simulator to recalibrate the breathalyzers themselves.

The traditional re-calibration system and procedure involves multiple transactions and/or communications among several entities. Typically an end user (general consumer, owner or operator of a breathalyzer) contacts the retailer from which the breathalyzer was purchased in order to report that the breathalyzer is in need of re-calibration. Currently, the large majority of all breathalyzer retailers are unable to perform re-calibration themselves, so either the retailer accepts breathalyzers requiring re-calibration from end users and ships them in bulk to a breathalyzer service center, or the retailer directs the end user to ship the breathalyzer requiring re-calibration directly to the service center. When the service center receives breathalyzers requiring re-calibration, detailed records of receipts, shipments, customer and retailer (vendor) data must be kept and maintained in order to minimize errors in processing and shipping the re-calibrated breathalyzer. Further, any problems that may arise are complicated to resolve, as these problems involve several parties that are not current with the specific situation of the end user (e.g. a single re-calibration may involve a retailer, distributor, service center and end user). With the multiple communications, transactions, record-keeping, processing and shipping that may be involved with each re-calibration, a steady increase in delays, costs and other problems can be seen in the breathalyzer market, because re-calibrations are unavoidable and periodically necessary.

In order to alleviate the time and utility lost when sending a breathalyzer for re-calibration, some end users purchase multiple breathalyzers so that at least one breathalyzer is available for use while one or more other devices are undergoing service for re-calibration. Some end users cannot afford the increase in budget in order to implement this type of stopgap measure, so compromises are made either in terms of temporary suspension of breath alcohol tests or over-taxing breathalyzer units beyond the point of necessary re-calibration (thereby allowing the breathalyzer to display increasingly inaccurate readings). In many cases, end users elect not to use breathalyzers altogether primarily due to the complications of re-calibration. Re-calibration, though an absolute necessity in the breathalyzer market, is one of the main impediments to rapid expansion of the market, especially in workplace, clinical or other professional environments where both accuracy and continuous utility are required.

Accordingly, the claimed invention proceeds upon the desirability of providing significant benefits for both the breathalyzer service centers and the end users by practically eliminating the loss of time and utility for end users and reducing the number of labor hours and shipping costs for service centers, all while introducing an effective solution at a cost no greater than the current service center system.

OBJECTS AND SUMMARY OF THE INVENTION

Therefore, it is an object of the claimed invention to provide a significantly improved replacement for the traditional method of breathalyzer re-calibration that supports market security by reducing or eliminating the time and utility lost by the end user and that also expands the market by addressing the specific needs of industrial or clinical breathalyzer applications.

It is a further object of the claimed invention to provide a calibrating breathalyzer which solves aforementioned problems with the current breathalyzer.

In accordance with an exemplary embodiment of the claimed invention, the calibrating breathalyzer comprises an alcohol sensor, a non-volatile memory, a processing unit or processor, a display and a housing to house these components. The alcohol sensor receives a breath air sample and measuring percent blood alcohol concentration (BAC %) based on analysis of the breath sample. The non-volatile memory stores calibration data of the alcohol sensor comprising one or more reference values within the BAC % range of the breathalyzer can analyze and display. The processing unit operates the breathalyzer in two modes. In the calibration mode, the processing unit calibrates the breathalyzer using the user's body as a simulator by receiving information regarding a metabolism rate of the user, type and amount of alcohol consumed by the user, and a drinking start time; determining maximum alcohol level from the type and amount of the alcohol consumed by the user; determining a sample time to receive a breath sample from the user based on a time to a predetermined calibration point from the drinking start time calculated using the metabolism rate of the user and the maximum alcohol level; receiving a BAC % measurement from the alcohol sensor based on the breath sample provided by the user at the sample time to provide a reference value; and storing the reference value as the calibration data in the breathalyzer. In the operation mode, the processing unit provides a BAC % reading based on the BAC % measurement by the alcohol sensor and the calibration data stored in the non-volatile memory. The processing unit displays the BAC % reading and other information for the user on the display.

In accordance with an exemplary embodiment of the claimed invention, the aforesaid processing unit of the breathalyzer alerts the user at a predetermined time before the sample time to provide the breath sample for calibrating the breathalyzer by an alarm, vibration, speaker, or a message on the display.

In accordance with an exemplary embodiment of the claimed invention, the aforesaid breathalyzer further comprises one or more buttons on the housing to input information about the type and amount of alcohol consumed by the user. The processing unit provides a list of alcohol types on the display for selection by the user using the buttons and stores the selection of the user in the non-volatile memory.

In accordance with an exemplary embodiment of the claimed invention, the aforesaid processing unit of the breathalyzer modifies the sample time by a predetermined lag time for alcohol to be present in user's circulatory system after alcohol consumption by the user.

In accordance with an exemplary embodiment of the claimed invention, the aforesaid processing unit of the breathalyzer determines the metabolism rate of the user based on the maximum alcohol level and BAC % measurements of the user's breath samples over a predetermined period of time.

In accordance with an exemplary embodiment of the claimed invention, the aforesaid processing unit of the breathalyzer receives BAC % measurement from the alcohol sensor based on the breath sample provided by the user at a predetermined interval until a statistically significant number of measurements are obtained to determine the metabolism rate of the user.

In accordance with an exemplary embodiment of the claimed invention, the aforesaid processing unit of the breathalyzer alerts the user to provide the breath sample at the predetermined interval by an alarm or a message on the display.

In accordance with an exemplary embodiment of the claimed invention, the aforesaid breathalyzer is one of the following: a portable breathalyzer, a coin-operated breathalyzer, a key-chain breathalyzer or a car ignition breathalyzer.

In accordance with an exemplary embodiment of the claimed invention, the aforesaid breathalyzer further comprises a heating unit to warm up the alcohol sensor to a predetermined temperature.

In accordance with an exemplary embodiment of the claimed invention, the aforesaid alcohol sensor of the breathalyzer detects changes in conductivity according to varying levels of alcohol concentration in said breath sample.

In accordance with an exemplary embodiment of the claimed invention, apparatus for calibrating a breathalyzer using a user's body as a simulator comprises an input device, a processor, a memory and a display. The input device receives information regarding a metabolism rate of the user, type and amount of alcohol consumed by the user, and a drinking start time. The processor determines a maximum alcohol level from the type and amount of the alcohol consumed by the user, determining a sample time to receive a breath sample by the breathalyzer from the user based on a time to a predetermined calibration point from the drinking start time calculated using the metabolism rate of the user and the maximum alcohol level. The processor receives a BAC % measurement taken by the breathalyzer based on the breath sample provided by the user at the sample time to provide a reference value. The memory stores the reference value in the breathalyzer. The processor displays the reference value to be inputted by the user into the breathalyzer on the display to provide a calibration data which is stored in the breathalyzer and used by the breathalyzer to provide BAC % reading to the user.

In accordance with an exemplary embodiment of the claimed invention, the aforesaid processor of the apparatus alerts the user at a predetermined time before the sample time to provide the breath sample to the breathalyzer by an alarm or a message on the display.

In accordance with an exemplary embodiment of the claimed invention, the aforesaid processor of the apparatus provides a list of alcohol types on the display for selection by the user using the input device and the memory stores the selection of the user.

In accordance with an exemplary embodiment of the claimed invention, the aforesaid processor of the apparatus modifies the sample time by a predetermined lag time for alcohol to be present in user's circulatory system after alcohol consumption by the user.

In accordance with an exemplary embodiment of the claimed invention, the aforesaid processor of the apparatus determines the metabolism rate of the user based on the maximum alcohol level and BAC % measurements of the user's breath samples taken by the breathalyzer over a predetermined period of time.

In accordance with an exemplary embodiment of the claimed invention, the aforesaid processor of the apparatus alerts the user to provide the breath sample to the breathalyzer at a predetermined interval by an alarm or a message on the display until a statistically significant number of measurements are obtained to determine the metabolism rate of the user.

In accordance with an exemplary embodiment of the claimed invention, the aforesaid apparatus is one of the following processor based device: a personal digital assistant, a smart phone, a tablet, a laptop, a personal computer, GPS navigation system and other comparable electronic device.

In accordance with an exemplary embodiment of the claimed invention, a non-transitory computer readable storage medium comprises computer executable code for calibrating of a breathalyzer using a user's body as a simulator. The code comprises instructions for the processor based device to (1) receive information regarding a metabolism rate of the user, type and amount of alcohol consumed by the user, and a drinking start time; (2) determine a maximum alcohol level from the type and amount of the alcohol consumed by the user by the processor based device, (3) determine a sample time to receive a breath sample by the breathalyzer from the user based on a time to a predetermined calibration point from the drinking start time calculated by the processor based device using the metabolism rate of the user and the maximum alcohol level; (4) receive a BAC % measurement taken by the breathalyzer based on the breath sample provided by the user at the sample time to provide a reference point; (5) store the reference point as an original reference point for a first calibration of the breathalyzer and as a new reference point for subsequent calibration of the breathalyzer; and (6) display the reference point to be inputted by the user into the breathalyzer to provide calibration data which is stored in the breathalyzer and used by the breathalyzer to provide BAC % reading to the user.

In accordance with an exemplary embodiment of the claimed invention, the aforesaid code further comprises instructions for alerting the user at a predetermined time before the sample time to provide the breath sample to the breathalyzer by an alarm or a message on the display of the processor based device.

In accordance with an exemplary embodiment of the claimed invention, the aforesaid code further comprises instructions for providing a list of alcohol types on the display of the processor based device for selection by the user and storing the selection of the user.

In accordance with an exemplary embodiment of the claimed invention, the aforesaid code further comprises instructions for determining the metabolism rate of the user based on the maximum alcohol level and a series of BAC % measurements of the user's breath samples taken by the breathalyzer over a predetermined period of time.

In accordance with an exemplary embodiment of the claimed invention, the aforesaid code further comprises instructions for alerting the user to provide the breath sample to the breathalyzer at a predetermined interval by an alarm or a message on the display of the processor based device until a statistically significant number of measurements are obtained to determine the metabolism rate of the user.

The traditional re-calibration system and procedure involves multiple transactions and/or communications among several entities. Typically an end user (general consumer, owner or operator of a breathalyzer) contacts the retailer from which the breathalyzer was purchased in order to report that the breathalyzer is in need of re-calibration. Currently, the large majority of all breathalyzer retailers are unable to perform re-calibration themselves, so either the retailer accepts breathalyzers requiring re-calibration from end users and ships them in bulk to a breathalyzer service center, or the retailer directs the end user to ship the breathalyzer requiring re-calibration directly to the service center. When the service center receives breathalyzers requiring re-calibration, detailed records of receipts, shipments, customer and retailer (vendor) data must be kept and maintained in order to minimize errors in processing and shipping the re-calibrated breathalyzer. Further, any problems that may arise are complicated to resolve, as these problems involve several parties that are not current with the specific situation of the end user (e.g. a single re-calibration may involve a retailer, distributor, service center and end user). With the multiple communications, transactions, record-keeping, processing and shipping that may be involved with each re-calibration, a steady increase in delays, costs and other problems can be seen in the breathalyzer market, because re-calibrations are unavoidable and periodically necessary.

Various other objects, advantages and features of the present invention will become readily apparent from the ensuing detailed description, and the novel features will be particularly pointed out in the appended claims.

BRIEF DESCRIPTION OF FIGURES

The following detailed descriptions, given by way of example, and not intended to limit the present invention solely thereto, will be best be understood in conjunction with the accompanying figures.

DETAILED DESCRIPTION OF THE EMBODIMENTS

The Breath Alcohol Testing Device is also commonly called a "breathalyser" or a "breathalyzer" (hereinafter breathalyzer), and includes both portable (PBT or Portable Breath Tester), stationary (coin-operated breathalyzer or similar) units, car engine immobilizing breath alcohol tester, and alcohol tester installed on other electronic device, such as a cell phone, a tablet, a lap-top, a personal digital assistant, a GPS navigation device, etc.

Figure 1:
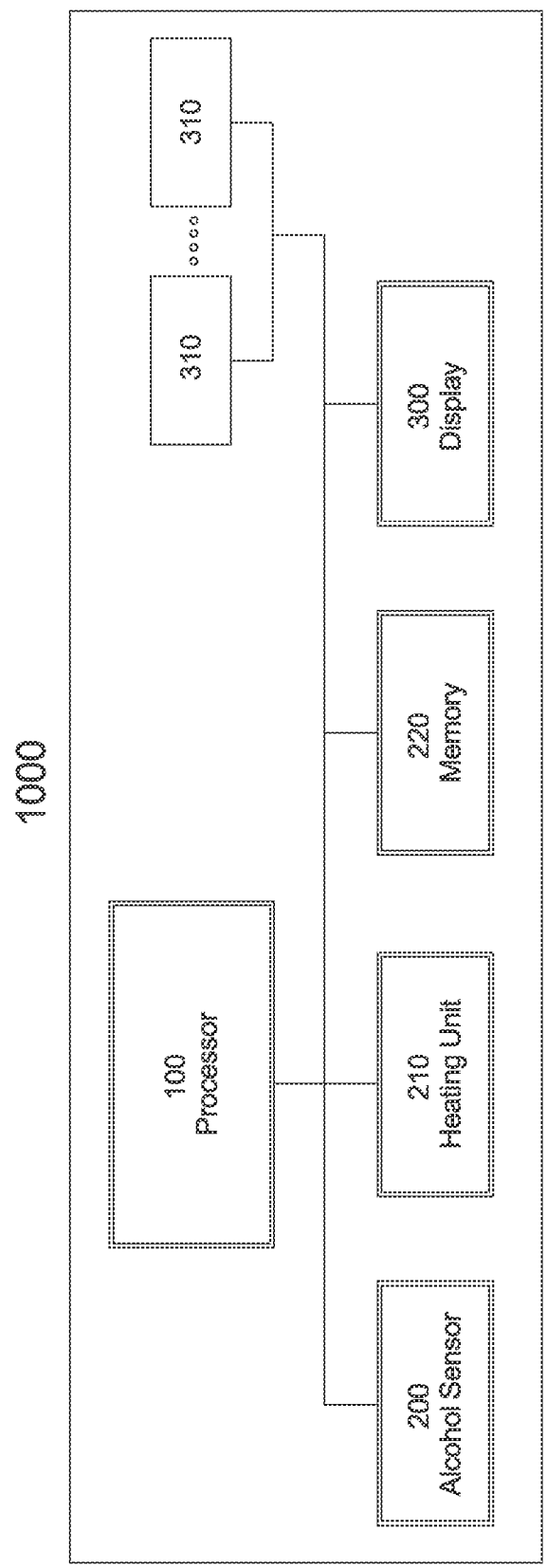
FIG. 1 is a diagram of a calibrating breathalyzer in accordance with an exemplary embodiment of the claimed invention.
Figure 2:
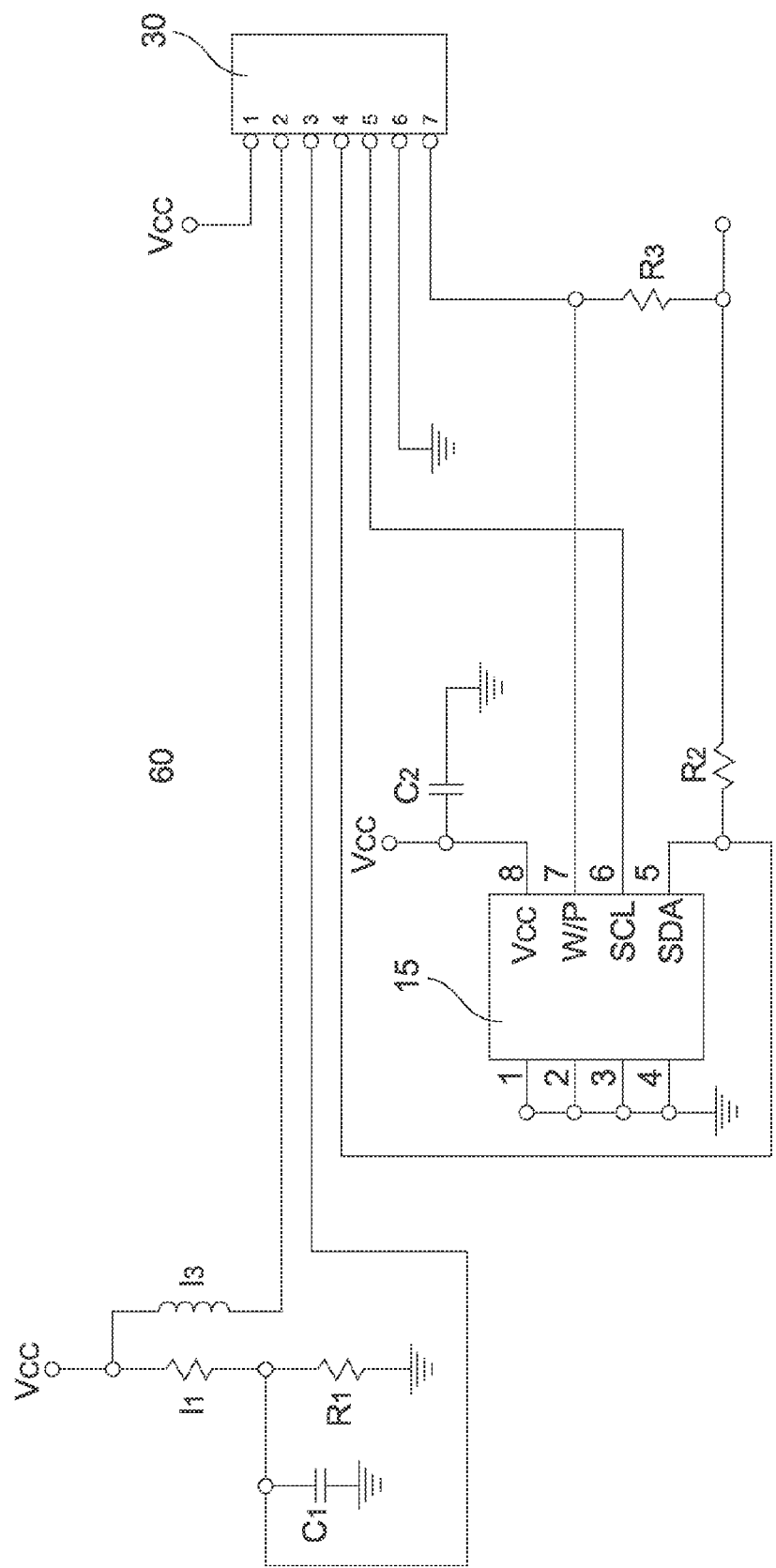
FIG. 2 is a diagram illustrating the primary circuitry of the alcohol sensor and non-volatile memory of the breathalyzer in accordance with an exemplary embodiment of the claimed invention.

Turning now to FIG. 1, in accordance with an exemplary embodiment of the claimed invention, the breathalyzer's processor, microcontroller, microprocessor, processing unit or signal processing unit 100 (collectively referred to herein as the "processor" or "processing unit") is connected to an alcohol sensor 200, a heating unit 210 and a non-volatile memory 220. As shown in FIG. 2, the sensor circuitry 11 of the alcohol sensor 200, a heating circuitry 13 of the heating unit 210 and a memory circuitry 15 of the non-volatile memory 220 are on a printed circuit board (PCB) 60 and connected to the CPU circuitry 30 of the processing unit 100. The non-volatile memory unit 220 can be EEPROM, flash drive, NAND and the like to store initial factory calibration data for the alcohol sensor 200. The sensor circuitry 11 of the alcohol sensor 200 is operable to detect changes in conductivity according to varying levels of alcohol concentration. The heating unit 210 is operable to warm up the alcohol sensor 200 to a predetermined temperature. The non-volatile memory unit 220 stores initial factory calibration data, which is used by the breathalyzer's processor or processing unit 100 to recalibrate the breathalyzer 1000. The memory circuitry 15 can include various pins, such as pin 7 labeled as "W/P," which means "write-protect," to prevent the non-volatile memory unit 220 from losing the calibration data.

The sensor circuitry 11 comprises a variable resistor which varies depending on how much alcohol is in the air near or in close proximity to the alcohol sensor 200. The more alcohol is in the air, the lower the resistance. That is, breathalyzer 1000 measures the alcohol in the breath by measuring the resistance. Instead of measuring the resistance, the breath alcohol sensor 200 can measure the voltage level between the sensor circuitry 11 and the load resistor R1. The sensor circuitry 11 and the load resistor essentially forms a voltage divider, and the lower the resistance of the sensor circuitry 11, the higher the sensor voltage reading. It is generally known that breath and blood alcohol content differ by a factor of 2100. That is, for every mg of alcohol in the breath, there are 2100 mg of alcohol in the blood. So BAC % (blood alcohol content or concentration percentage) equals breath mg/L*0.21. Accordingly, the non-volatile memory 220 additionally stores sensor voltage readings and resistance measurements of various predetermined BAC % and breath mg/L.

Returning to FIG. 2, in accordance with an exemplary embodiment of the claimed invention, the breathalyzer's processor or processing unit 100 communicates with the sensor circuitry 11 through a pin 3 and communicates with the memory circuit 15 through pins 4 and 5 to retrieve, e.g., the calibration data from the non-volatile memory 220.

Typically, the user purchases the breathalyzer 1000 for work (e.g., a police officer can use it for sobriety testing), clinical studies, personal use, etc. After many repeated uses, the breathalyzer generally requires re-calibration due to electrical drifting of one or more components of the alcohol sensor 200 and/or other problems discussed herein. Typically, the breathalyzer 1000 requires re-calibration after being used for 200-2000 times (varying depend on the type of alcohol sensor and other factors noted herein). Alternatively, the alcohol sensor 200 or the processing unit 100 of the breathalyzer can perform tests periodically or upon request by the operator (i.e., pressing a button 310 or using a pin hole 310 on the housing of the breathalyzer) to determine if the alcohol sensor 200 requires re-calibration. An inquiry is made to determine if the breathalyzer 1000 requires re-calibration. If the inquiry is answered in the negative, the breathalyzer 1000 can be used to calculate or measure BAC %. However, if the inquiry is answered in the affirmative, the user can initiate re-calibration of the breathalyzer 1000. Alternatively, the user is alerted by an alarm or a message on the LED or LCD display 300 on the breathalyzer 1000 indicating that the breathalyzer 1000 requires recalibration, and the user can initiate re-calibration by pressing a button on the housing of the breathalyzer 1000 or inputting yes to re-calibration when prompted by the message on the LED or LCD display 300 on the breathalyzer 1000.

In accordance with an exemplary embodiment of the claimed invention, when the user initiates re-calibration, the breathalyzer 1000 enters a calibration mode. In the calibration mode, the processor or processing unit 100 reads the initial factory calibration data for the alcohol sensor 200 from the non-volatile memory 220. The initial factory calibration data can include one or more predetermined BAC's %, and corresponding sensor voltage measurements and resistance measurements. For each predetermined BAC %, the breathalyzer 1000 applies the corresponding stored sensor voltage, and then measures the resistance. If the measured resistance is different from the stored resistance measurement for one or more predetermined BAC %'s, then the processor/processing unit 100 recalibrates the breathalyzer 1000 by adjusting the correspondence or relationship between the BAC %, resistance and the sensor voltage. Further, the processor/processing unit 100 replaces the stored resistance measurement in the non-volatile memory 220 with the measured resistance value. Alternatively, for each predetermined BAC %, the breathalyzer 1000 applies the corresponding stored resistance, and then measures the sensor voltage. If the measured sensor voltage is different from the stored sensor voltage measurement for one or more predetermined BAC's %, then the processor/processing unit 100 recalibrates the breathalyzer 1000 by adjusting the correspondence or relationship between the BAC %, the resistance, and the sensor voltage. Further, the processor/processing unit 100 replaces the stored sensor voltage measurement in the non-volatile memory 220 with the measured sensor voltage value.

In accordance with an exemplary embodiment of the claimed invention, the calibrating breathalyzer 1000 determines the change in the relationship between BAC %, resistance and sensor voltage. The breath alcohol sensor measurement is then recalibrated to account for this change in the relationship between BAC % resistance and sensor voltage.

In accordance with an exemplary embodiment of the claimed invention, the calibrating breathalyzer 1000 can be recalibrated by the end user without requiring any special tools (e.g., simulator with either standard alcohol solution(s) or dry gas) or without utilizing third party services. The claimed calibrating breathalyzer 1000 essentially utilizes the human body as the simulator and operator's breadth air after consumption of predetermined volume of alcohol (e.g., BAC %) as the standard alcohol solution or dry gas, thereby eliminating the current inefficient and costly calibration process. As soon as one drinks alcohol, the alcohol moves within the body through the circulatory system. As the body begins to metabolize the alcohol based on the user's metabolism rate, the alcohol level in the body decreases gradually over time. The processor 100 predicts or determines how long after the consumption of the alcohol (hereinafter the "elapsed time"), the user's breath will contain approximately one of the predetermined BACs % based on the user's metabolism rate. It is appreciated that the required calibration points can be predetermined at the factory or established by the user before initiating the self-calibration process. The claimed breathalyzer 1000 can employ one or more calibration values or points, e.g., 0.005 BAC %, 0.01 BAC %, etc. That is, the claimed invention proceeds upon the desirability of utilizing the end user's or operator's body as a simulator or cylinder by recording and/or determining the period of time required to reach the predetermined calibration point(s) after consuming the predetermined volume (and/or level) of alcohol.

In accordance with an exemplary embodiment of the claimed invention, after receiving the information regarding the type, amount and time of the alcohol consumed by the user, the processor 100 sets the timer to zero and alerts the user to provide a breath sample when the timer nears the elapsed time. The processor 100 stores the measured BAC % as a reference value or a calibration data in the non-volatile memory 220 and provides BAC % measurement during the normal operation mode based on linear calculation using the stored reference point or calibration data. Details of BAC % calculation are set forth in a document issued by the DOR/ NHTSA on October 1994, entitled "Computing of BAC Estimate," which is incorporated herein in its entirety. The processor 100 repeats this process other predetermined BAC % or calibration points. For example, if there are two predetermined calibration points, then the processor 100 determines the elapsed time 1 for the first calibration point and the elapsed time 2 for the second calibration point based on the user's metabolism rate. The processor 100 sets the timer to zero and alerts the user to provide a first breath sample when the timer nears the elapsed time 1 and a second breath sample when the timer nears elapsed time 2. The processor 100 stores the measured BAC's % at these two elapsed times as reference points in the non-volatile memory 220 and provides BAC % measurement during the normal operation mode based on linear calculation using the stored reference points. It is appreciated that the maximum BAC % for calibration must exceed the highest reference point.

Typically, the user purchases the breathalyzer for work (e.g., a police officer can use it for sobriety testing), clinical studies, personal use, etc. After many repeated uses, the breathalyzer generally requires re-calibration as discussed herein. When the standard breathalyzer requires re-calibration, the user contacts the retailer and the retailer directs the user to an appropriate service center. The user then ships the standard breathalyzer to the service center for re-calibration. Upon receipt of the standard breathalyzer, the service center calibrates the standard breathalyzer, e.g., using the simulation system, and ships the re-calibrated breathalyzer back to the user, thereby enabling the user use the standard breathalyzer to calculate or measure BAC %.

In accordance with an exemplary embodiment of the claimed invention, after consuming predetermined volume and/or level of alcohol, the user can operate the claimed breathalyzer 1000 in the calibration mode to initiate the calibration of the claimed breathalyzer 1000. In the calibration mode, the processor 100 self-calibrates the breathalyzer 1000 utilizing the user's body as a simulator based on information received from the user. After consuming the alcohol, the user enters the type and amount of alcohol consumed, e.g., one 12 ounce bottle or can of beer (5% alcohol by volume), one 5 ounce glass of wine (12% alcohol by volume) or one 1.5 ounce shot of hard liquor (40% alcohol by volume), etc., into the breathalyzer 100 using the buttons or pin holes 310. Preferably the user selects the type of alcohol consumed from a list on the display 300 using the buttons/pin holes 310 and enters the amount, e.g., two 12 ounce cans of beer, and how long ago (i.e., time elapsed between the consumption of the alcohol and entry of such information into the breathalyzer 1000). That is, the processor 100 displays a list of alcohol types on the display 300 and the user selects the type of alcohol consumed using the buttons/pin holes 310. The processor 100 stores the user's selection in the non-volatile memory 220, and requests the user to enter the number, volume or amount of the selected alcohol consumed by the user on the display 300, which is also stored in the non-volatile memory 220. Further, the user enters the time when the user started drinking the selected alcohol or the start time into the breathalyzer 1000 using the buttons 310. In accordance with an exemplary aspect of the claimed invention, the processor 100 determines the total drinking time in minutes. Since it takes time before alcohol circulates in the user's blood after consumption, this lag time, which is generally approximately 5-10 minutes, is used to modify the start time. The processor uses the modified start time to set timer to zero in measuring/calculating the elapsed time(s) for the calibration point(s).

In accordance with an exemplary embodiment of the claimed invention, the processor 100 calculates or receives the user's metabolism rate and stores it in the non-volatile memory 220, preferably, this is performed before the breathalyzer 1000 is used for the first time. After consuming the alcohol, the user enters the type and amount of alcohol consumed, e.g., one 12 ounce bottle or can of beer (5% alcohol by volume), one 5 ounce glass of wine (12% alcohol by volume) or one 1.5 ounce shot of hard liquor (40% alcohol by volume), etc., into the breathalyzer 100 using the buttons 310. Preferably the user selects the type of alcohol consumed from a list on the display 300 using the buttons 310 and enters the amount, e.g., two 12 ounce cans of beer. That is, the processor 100 displays a list of alcohol types on the display 300 and the user selects the type of alcohol consumed using the buttons 310. The processor 100 stores the user's selection in the non-volatile memory 220, and requests the user to enter the number, volume or amount of the selected alcohol consumed by the user on the display 300, which is also stored in the non-volatile memory 220. As the body begins to metabolize the alcohol, the alcohol level in the body decreases gradually over time based on the user's metabolism rate. The processor 100 can determine the maximum alcohol level from the type and amount of alcohol consumed by the user, e.g., two 12 ounce cans of beer or one 1.5 ounce shot of hard liquor, etc. After receiving the user's entry regarding the alcohol consumption, the processor 100 periodically, e.g., every five or ten minutes, requests the user to provide the breath samples until sufficient number of measurements are obtained. It is appreciated that the range of BAC % measurements should be statistically significant to determine the user's metabolism rate. The processor 100 can determine the user's metabolism rate based on the maximum alcohol level and the BAC % measurements. That is, since the decrease in user's BAC % measurements (i.e., percent alcohol in the user's blood) correlates with user's metabolism rate, the processor 100 can determine the user's metabolism rate from the change and/or the rate of change in percent alcohol in the user's blood or BAC % measurements over time. It is appreciated that the processor 100 can employ other known methodologies to determine the user metabolism rate, such as based on user's weight, gender, frequency of alcohol consumption and personal variation.

After many repeated uses of the breathalyzer 100 to calculate or measure BAC %, the breathalyzer 1000 generally requires re-calibration as discussed herein. Typically, the breathalyzer 1000 requires re-calibration after being used for 100-3000 times (varying depend on the factors noted herein). Alternatively, the alcohol sensor 200 or the processing unit 100 of the breathalyzer 1000 can perform tests periodically or upon request by the operator (i.e., pressing a button on the housing of the breathalyzer 1000) to determine if the alcohol sensor 200 requires re-calibration. The user can initiate self-calibration by operating the breathalyzer 1000 in the calibration mode. As noted herein, after consuming the alcohol, the user enters the type and amount of alcohol consumed, e.g., two 5 ounce glasses of wine or one 1.5 ounce shot of hard liquor, into the breathalyzer 100 using the buttons 310. Preferably the user selects the type of alcohol consumed from a list on the display 300 using the buttons 310 and enters the amount, e.g., two 12 ounce cans of beer, and how long ago (i.e., time elapsed between the consumption of the alcohol and entry of such information into the breathalyzer 1000). That is, the processor 100 displays a list of alcohol types on the display 300 and the user selects the type of alcohol consumed using the buttons 310. The processor 100 stores the user's selection in the non-volatile memory 220, and requests the user to enter the number, volume or amount of the selected alcohol consumed by the user on the display 300, which is also stored in the non-volatile memory 220. Further, the user enters the time when the user started drinking the selected alcohol or the start time into the breathalyzer 1000 using the buttons 310. The processor 100 uses the start time modified by the lag time to set the timer to zero in measuring/calculating the elapsed time(s) for the calibration point(s).

As the body begins to metabolize the alcohol based on the user's metabolism rate, the alcohol level in the body decreases gradually over time. Based on the information received from the user regarding the consumed alcohol, the processor 100 can determine the maximum alcohol level. Based on the user's stored metabolism rate and information received from the user regarding the consumed alcohol, the processor 100 can determine the elapsed time before the user's breath will contain one of the calibration points or predetermined BAC %. The claimed breathalyzer 1000 can employ one or more calibration points, e.g., 0.005 BAC %, 0.01 BAC %, etc.

In accordance with an exemplary embodiment of the claimed invention, after receiving the information regarding the type, amount and time of the alcohol consumed by the user, the processor 100 sets the timer to zero and alerts the user to provide a breath sample when the timer nears the elapsed time. The processor 100 stores the measured BAC % as a new reference point or calibration data in the non-volatile memory 220 and provides BAC % measurement during the normal operation mode based on linear calculation using the reference point(s) stored in the non-volatile memory 220. Although one calibration point is used in this example, it is appreciated that more than calibration point can be used to obtain multiple new reference points. The processor 100 provides BAC % measurement during the normal operation mode based on linear calculation using the new and original reference points.

Figure 3:
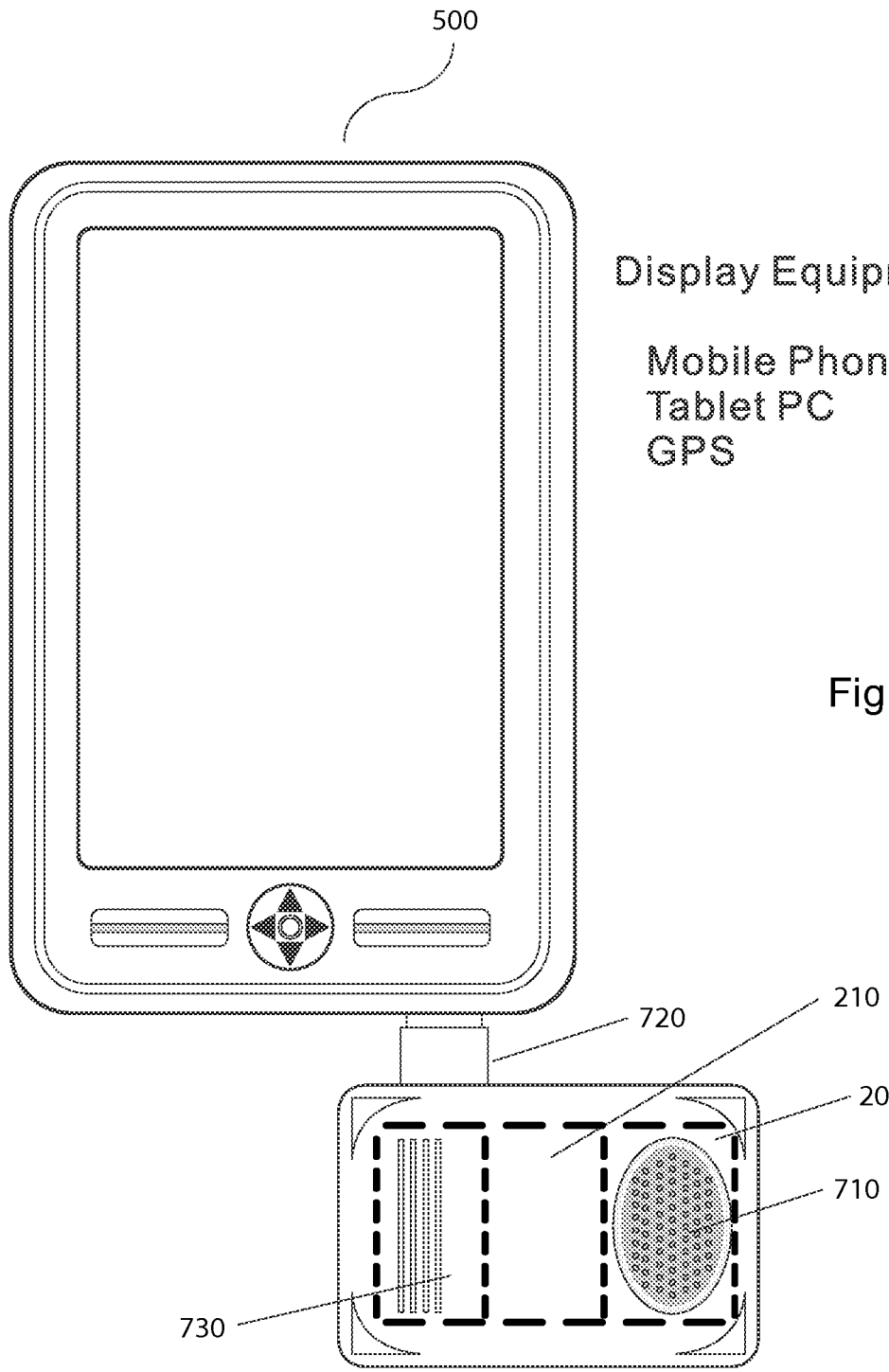
FIG. 3 is a diagram of a calibrating apparatus for calibrating a standard breathalyzer in accordance with an exemplary embodiment of the claimed invention.

Turning now to FIG. 3, in accordance with an exemplary embodiment of the claimed invention, apparatus 500 for calibrating a standard breathalyzer 600 using a user's body as a simulator comprises an input device 510, a processor 520, a memory 530 and a display 540. It is appreciated that the calibrating apparatus 500 can be any processor based device, such as a personal digital assistant, a smart phone, a tablet, a laptop, a personal computer, a GPS navigation device, a digital camera and the like. The input device 510, such as a keyboard, touchpad, mouse, buttons and the like, receives information regarding a metabolism rate of the user, type and amount of alcohol consumed by the user, and a drinking start time. Preferably, the processor 520 of the apparatus 500 provides a list of alcohol types on the display 540 for selection by the user using the input device 510 and the memory 530 stores the selection of the user. The processor 520 determines a maximum alcohol level from the type and amount of the alcohol consumed by the user. The processor 520 also determines a sample time to receive a breath sample by the breathalyzer 600 from the user based on a time to a predetermined calibration point from the drinking start time calculated using the metabolism rate of the user and the maximum alcohol level. Preferably, the processor 520 modifies the sample time by a predetermined lag time, e.g., 5 to 10 minutes, for the alcohol to be present in user's circulatory system after the alcohol is consumed by the user. The processor 520 receives a BAC % measurement taken by the breathalyzer 600 based on the breath sample provided by the user at the sample time to provide a reference point. Preferably, the processor 520 alerts the user at a predetermined time before the sample time to provide the breath sample to the breathalyzer 600 by an alarm or a message on the display 540. The memory 530 stores the reference point for use as a calibration data by the breathalyzer 600. The display 540 presents the reference point to be inputted by the user into the breathalyzer 600 to provide a calibration data which is stored in the breathalyzer 600 and used by the breathalyzer 600 to provide BAC % readings for the breath samples.

In accordance with an exemplary embodiment of the claimed invention, the processor 520 of the apparatus 500 can determine the metabolism rate of the user based on the maximum alcohol level and BAC % measurements of the user's breath samples taken by the breathalyzer 600 over a predetermined period of time, e.g., 1-3 hours, until one or more predetermined BAC % measurements or calibration points are reached. The processor 520 can alert the user to provide the breath sample to the breathalyzer 600 at a predetermined interval by an alarm or a message on the display 540 until a statistically significant number of measurements are obtained to determine the metabolism rate of the user.

In accordance with an exemplary embodiment of the claimed invention, a non-transitory computer readable storage medium, such as DVD, CD, memory stick, USB drive, and other known storage device, comprises computer executable code for calibrating of a breathalyzer 600 using a user's body as a simulator. The code comprises instructions for the processor based device 500 to (1) receive information regarding a metabolism rate of the user, type and amount of alcohol consumed by the user, and a drinking start time; (2) determine a maximum alcohol level from the type and amount of the alcohol consumed by the user by the processor based device 500; (3) determine a sample time to receive a breath sample by the breathalyzer 600 from the user based on a time to a predetermined calibration point from the drinking start time calculated by the processor based device 500 using the metabolism rate of the user and the maximum alcohol level; (4) receive a BAC % measurement taken by the breathalyzer 600 based on the breath sample provided by the user at the sample time to provide a reference point; (5) store the reference value/point; and (6) display the reference point to be inputted by the user into the breathalyzer 600 to provide a calibration data which is stored in the breathalyzer 600 and used by the breathalyzer 600 to provide BAC % readings for the breath samples.

Figure 5:
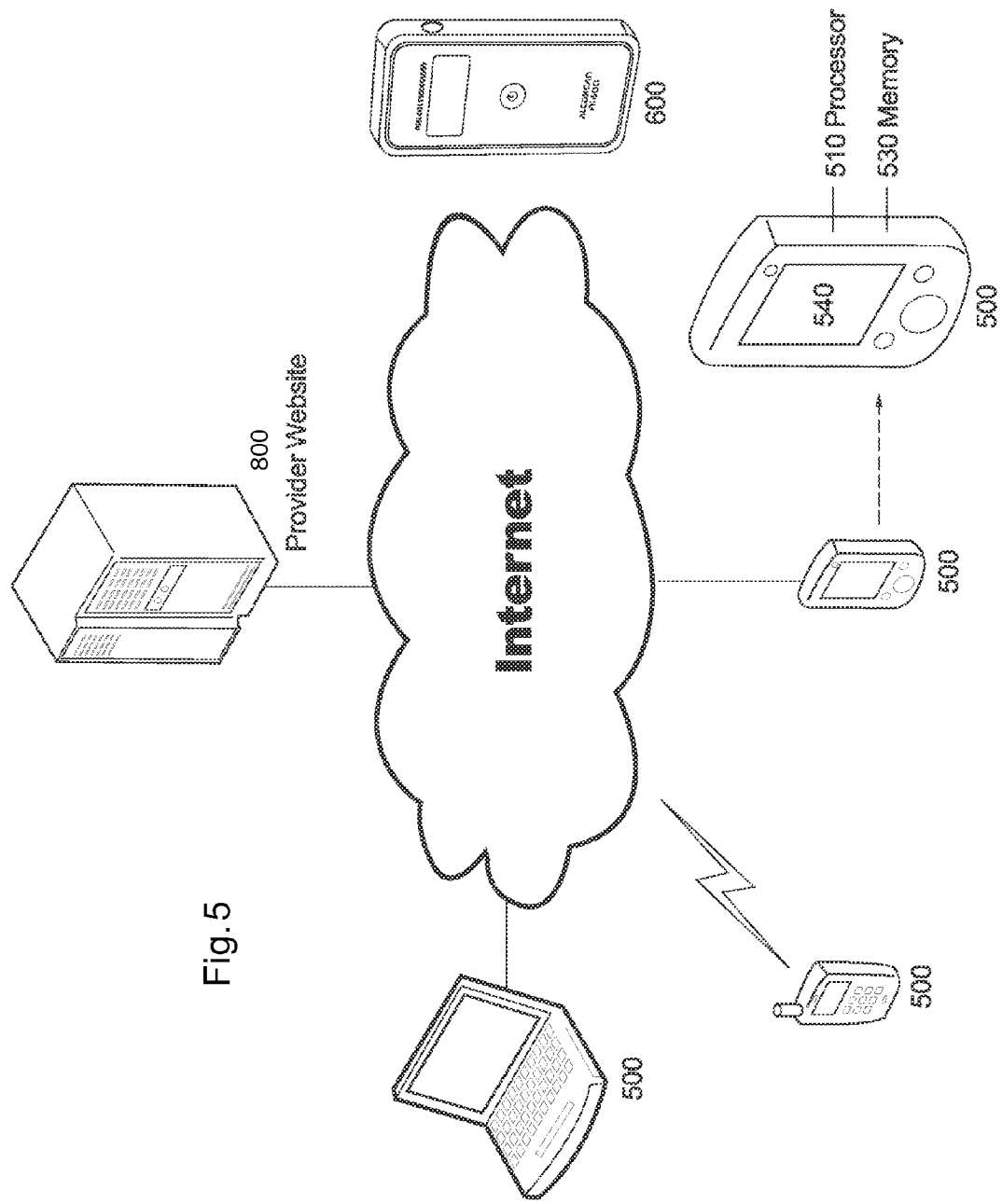
FIG. 5 is a diagram of a communication network incorporating a web-based calibrating apparatus in accordance with an exemplary embodiment of the claimed invention.

In accordance with an exemplary embodiment of the invention, the computer executable code can be downloaded from a provider's website or web server 800 via a communications network or Internet, as shown in FIG. 5 or installed from a computer readable storage medium to a processor based device 500 to calibrate the standard breathalyzer 600 using the user's or operator's body as a simulator. The processor based device 500 can be a personal digital assistant, a cell or smart phone, a tablet, a laptop, a personal computer, a GPS navigation device, a digital camera or other comparable devices.

In accordance with an exemplary embodiment of the claimed invention, as shown in FIGS. 1-3, an alcohol testing unit 700 comprises at least the alcohol sensor 200, and a sensor cover 710 comprising a plurality of holes and an input/output port 720. Additionally, the alcohol testing unit 700 can comprises one or more buttons/pin holes 310 and/or a heating unit 210. The alcohol testing unit 700 communicates with the processor based device 500 via the input/output port 720. It is appreciated that input/output port 720 can be any standard computer interface, such as universal serial bus (USB) connector 720. Although, not shown, the alcohol testing unit 700 can further comprises a communication unit 730 to wirelessly communicate with the processor based device 500 over a wireless network, Wi-Fi, Wi-Max, Bluetooth and the like. The user provides a breath sample to the alcohol testing unit 700 by blowing through the sensor cover 710 and onto the alcohol sensor 200 positioned behind the sensor cover 710. It is appreciated that the alcohol sensor 200 can be located elsewhere in the alcohol testing unit 700 and the user's breath sample can be directed to the alcohol sensor 200 via an optional air tube (not shown). The alcohol sensor 200 provides the BAC % measurement to the processor based device 500 running a breathalyzer application/program which can be downloaded onto the processor based device 500 from the provider's website/web server 800 or loaded from the non-transitory computer readable storage medium. That is, the claimed invention can convert any processor based electronic device 500 into a breathalyzer utilizing the alcohol testing unit 700 and the breathalyzer application/program. The external alcohol testing unit 700 can be re-calibrated using the user's body as a simulator as described herein.

Figure 4:
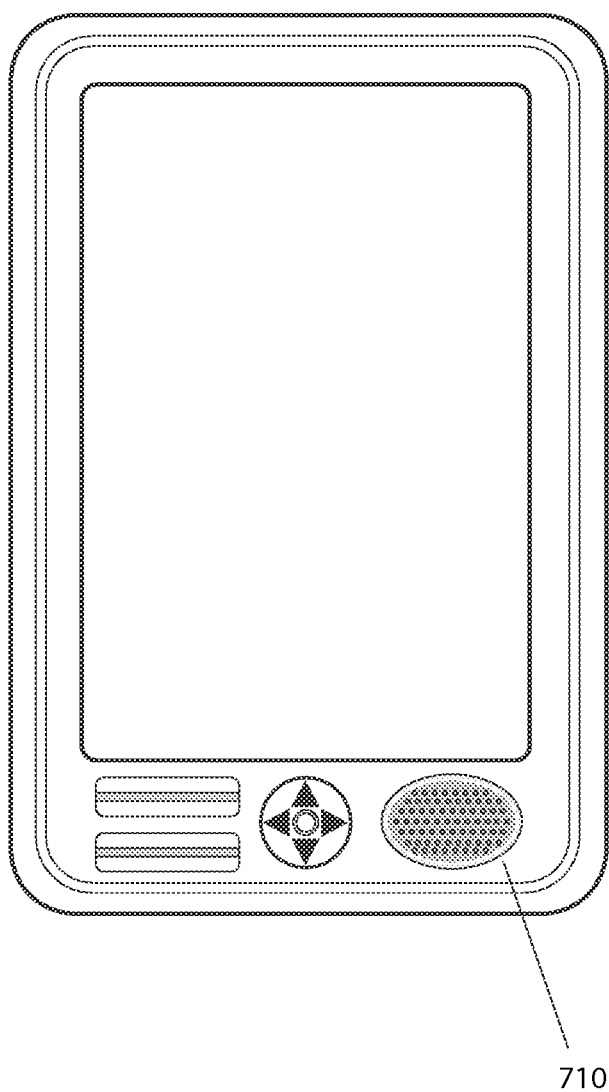
FIG. 4 is a diagram of a processor based device incorporating the calibrating breathalyzer in accordance with an exemplary embodiment of the claimed invention.

In accordance with an exemplary embodiment of the claimed invention, the processor based device 500 comprises a built-in or internal alcohol testing unit 700, thereby eliminating the need to connect (e.g., via a wireless or wired connection) the external alcohol testing unit 700 to the processor based device 500. The processor based device 500 can be utilized both as a breathalyzer and a cell phone, a tablet, a GPS navigation system, a laptop, a PC, a digital camera, a personal digital assistant, etc. As shown in FIGS. 1, 2 and 4, the user provides a breath sample to the processor based device 500 through the sensor cover 710 and onto the alcohol sensor 200 positioned behind the sensor cover 710. It is appreciated that the alcohol sensor 200 can be located elsewhere in the alcohol testing unit 700 and the user's breath sample can be directed to the alcohol sensor 200 via an optional air tube (not shown). The built-in or internal alcohol testing unit 700 can be re-calibrated using the user's body as a simulator as described herein.

In accordance with an exemplary embodiment of the claimed invention, the user can access and utilize a calibration application from the provider's website or web server 800 to calibrate the breathalyzer using a web-enabled client device 500, such as a laptop, a tablet, a cell or smart phone, a personal digital assistant, etc. After invoking the calibration application, using the web-enabled client device 500, the user enters information regarding the user's metabolism rate, type and amount alcohol consumed by the user, and the drinking start time. Preferably, the web server 800 provides a list of alcohol types to the web-enabled client device 500 to display on the display 540 for selection by the user using the input device 510 of the web-enabled client device 500. The user's selection can be stored in the memory of the web-enabled client device and/or the web server 800. The web-enabled client device 500 transmits the entered information to the web server 800 over the Internet.

The web server 800 determines a maximum alcohol level from the type and amount of the alcohol consumed by the user. The web server 800 also determines a sample time to receive a breath sample by the breathalyzer 600 from the user based on a time to a predetermined calibration point from the drinking start time calculated using the metabolism rate of the user and the maximum alcohol level. Preferably, the web server 800 modifies the sample time by a predetermined lag time, e.g., 5 or 10 minutes, for the alcohol to be present in user's circulatory system after the alcohol is consumed by the user. The web server 800 receives a BAC % measurement taken by the breathalyzer 600 based on the breath sample provided by the user at the sample time to provide a reference point. Preferably, the web server 800 instructs the web-enabled client device 500 to alert the user at a predetermined time before the sample time to provide the breath sample to the breathalyzer 600 by an alarm or a message on the display 540. The memory of the web-enabled client device 500 and/or web server 800 stores the reference point for use as a calibration data by the breathalyzer 600. The display 540 presents the reference point to be inputted by the user into the breathalyzer 600 to provide a calibration data which is stored in the breathalyzer 600 and used by the breathalyzer 600 to provide BAC % readings for the breath samples.

The present invention, having been described, will make apparent to those skilled in the art that the same may be varied in many ways without departing from the spirit and scope of the invention. Any and all such modifications are intended to be included within the scope of the following claims.

What is claimed is:

1. A calibrating breathalyzer, comprising:
an alcohol sensor for receiving a breath air sample and measuring percent blood alcohol concentration (BAC %) based on analysis of the breath sample;
a non-volatile memory for storing calibration data of the alcohol sensor comprising one or more reference points;
a processing unit for operating the breathalyzer in two modes: (A) a calibration mode to calibrate the breathalyzer using a user's body as a simulator by receiving a BAC % measurement from the alcohol sensor based on the breath sample provided by a user at a sample time to provide a reference point, the sample time determined based on a user's metabolism rate; and storing the reference point; and (B) an operation mode to provide a BAC % reading based on the BAC % measurement by the alcohol sensor and the calibration data stored in the non-volatile memory;
a display for displaying the BAC % reading and other information to a user; and
a housing to house the processing unit, the alcohol sensor, the non-volatile memory and the display.

2. The calibrating breathalyzer of claim 1, further comprising an input device for receiving information about type and amount of alcohol consumed by the user, and a drinking start time; wherein the processing unit provides a list of alcohol types on the display for selection by the user using the input device and stores the selection of the user in the non-volatile memory; and wherein the processing unit determines a maximum alcohol level from the type and amount of alcohol consumed by the user, and determines the user's metabolism rate based on the maximum alcohol level and BAC% measurement over a predetermined period of time.

3. The calibrating breathalyzer of claim 2, wherein the processing unit alerts the user at a predetermined time before the sample time to provide the breath sample for calibrating the breathalyzer by an alarm or a message on the display; and wherein the processing unit receives BAC % measurements from the alcohol sensor based on the breath samples provided by the user at a predetermined interval until a statistically significant number of measurements are obtained to determine the user's metabolism rate.

4. The calibrating breathalyzer of claim 2, wherein the processing unit determines the sample time to receive the breath sample from the user based on a time to a predetermined calibration point from the drinking start time calculate using the user's metabolism rate and the maximum alcohol level; and wherein the processing unit modifies the sample time by a predetermined lag time for alcohol to be present in user's circulatory system after alcohol consumption by the user.

5. The calibrating breathalyzer of claim 1, wherein the breathalyzer is one of the following: a portable breathalyzer, a coin-operated breathalyzer, a key-chain breathalyzer, or a car ignition breathalyzer.

6. The calibrating breathalyzer of claim 1, wherein the breathalyzer is one of a following processor based device: a tablet, a laptop, a personal computer, a cell phone, a GPS navigation device, a digital camera or a personal digital assistant.

7. The calibrating breathalyzer of claim 6, further comprising an external alcohol testing unit comprising the alcohol sensor and at least one of the following: a communications unit to wirelessly communicate BAC % measurement to the processing unit of the processor based device or a USB connector to communicate with the processing unit via a USB port of the processor based device.

8. Apparatus for calibrating a breathalyzer using a user's body as a simulator, comprising:
  a processor for receiving a percent blood alcohol concentration (BAC %) measurement from an alcohol sensor based on the breath sample provided by the user at a sample time to provide a reference point, the sample time determined based on a user's metabolism rate and a time to a predetermined calibration point;
  a memory for storing the reference point; and
  a display for displaying the reference point to be inputted by the user as a calibration data into the breathalyzer.

9. The apparatus of claim 8, further comprising an input device for receiving information about type and amount of alcohol consumed by the user, and a drinking start time; and wherein the processor provides a list of alcohol types on the display for selection by the user using the input device, stores the selection of the user in the memory, determines a maximum alcohol level from the type and amount of alcohol consumed by the user, and determines the user's metabolism rate based on the maximum alcohol level and BAC % measurement taken by the breathalyzer over a predetermined period of time.

10. The apparatus of claim 9, wherein the processor alerts the user at a predetermined time before the sample time to provide the breath sample to the breathalyzer by an alarm or a message on the display; and wherein the input device receives BAC % measurements of the breath samples provided to the breathalyzer by the user at a predetermined interval until a statistically significant number of measurements are obtained to determine the user's metabolism rate.

11. The apparatus of claim 10, further comprising a communications unit to provide a wired or wireless communication with the breathalyzer; and wherein the processor receives BAC % measurements from the breathalyzer via the communications unit.

12. The apparatus of claim 9, wherein the processor determines the time to the predetermined calibration point from the drinking start time based on the user's metabolism rate and the maximum alcohol level; and wherein the processor modifies the sample time by a predetermined lag time for alcohol to be present in user's circulatory system after alcohol consumption by the user.

13. The apparatus of claim 8, wherein the apparatus is one of a following processor based device: a tablet, a laptop, a personal computer, a cell phone, a GPS navigation device, a digital camera or a personal digital assistant.

14. Apparatus for calibrating breathalyzer using a user's body as a simulator, comprising:
  a web server comprising:
    a processor for receiving a percent blood alcohol concentration (BAC %) measurement from an alcohol sensor based on the breath sample provided by the user at a sample time to provide a reference point, the sample time determined based on a user's metabolism rate; and
    a memory for storing the reference point;
  a web-enabled client device comprising:
    an input device to receive information from the user; and
    a display for displaying the reference point to be inputted by the user as a calibration data into the breathalyzer;
  wherein the web-enabled client device is used to access the web server over the Internet to calibrate the breathalyzer.

15. The apparatus of claim 14, wherein the web-enabled client device is one of a following processor based device: a tablet, a laptop, a personal computer, a cell phone, a GPS navigation device, a digital camera or a personal digital assistant.

16. Apparatus for calibrating breathalyzer using a user's body as a simulator, comprising:
  a web server comprising a processor for receiving a percent blood alcohol concentration (BAC %) measurement from an alcohol sensor based on the breath sample provided by the user at a sample time to provide a reference point, the sample time determined based on a user's metabolism rate;
  a web-enabled client device comprising:
    a memory for storing the reference point;
    an input device to receive information from the user;
    a memory for storing the reference point; and
    a display for displaying the reference point to be inputted by the user as a calibration data into the breathalyzer;
  wherein the web-enabled client device is used to access the web server over the Internet to calibrate the breathalyzer.

17. The apparatus of claim 16, wherein the web-enabled client device is one of a following processor based device: a tablet, a laptop, a personal computer, a cell phone, a GPS navigation device, a digital camera or a personal digital assistant.

18. A computer based method for calibrating of a breathalyzer using a user's body as a simulator, comprising the steps of:
  determining by a processor based device a sample time to receive a breath sample by the breathalyzer from the user based on a user's metabolism rate and a time to a predetermined calibration point;
  receiving by the processor based device a percent blood alcohol concentration (BAC %) measurement taken by the breathalyzer based on the breath sample provided by the user at a sample time to provide a reference point;
  storing the reference point in a memory of the processor based device; and
  displaying the reference point to be inputted by the user as a calibration data into the breathalyzer.

19. The method of claim 18, further comprising the steps of:
  receiving information regarding type and amount of alcohol consumed by the user, and a drinking start time by a processor based device;
  determining a maximum alcohol level from the type and amount of the alcohol consumed by the user by the processor based device;
  determining the metabolism rate of the user based on the maximum alcohol level and a series of BAC % measurements of the user's breath samples taken by the breathalyzer over a predetermined period of time; and alerting the user to provide the breath sample to the breathalyzer at a predetermined interval by an alarm or a message on the display of the processor based device until a statistically significant number of measurements are obtained to determine the metabolism rate of the user.

20. The method of claim 19, further comprising the step of determining the time to the predetermined calibration point from the drinking start time by the processor based device using the user's metabolism rate and the maximum alcohol level.

* * * * *